United States Patent [19]

Zaiger et al.

[11] Patent Number: Plant 6,755

[45] Date of Patent: Apr. 25, 1989

[54] APRICOT TREE ("TRI-GEMS")

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 142,491

[22] Filed: Jan. 11, 1988

[51] Int. Cl.[4] ..... A01H 5/00

[52] U.S. Cl. ..... Plt./39

[58] Field of Search ..... Plt./39

*Primary Examiner*—James R. Feyrer

[57] ABSTRACT

Our new and distinct variety of apricot tree has the following unique combination of desirable features:

1. Heavy and regular production of fruit.
2. Very firm fruit that will mechanically harvest without excessive bruising.
3. Fruit that will maintain excellent texture, shape and appearance after being canned.
4. Fruit with good flavor and eating quality both fresh and canned.
5. Fruit with a high degree of soluble solids (Average 15% Brix).
6. Vigorous, semi-spreading growth.
7. Fruit with excellent storage and shipping quality.

1 Drawing Sheet

ORIGIN OF THE VARIETY

Our new variety of apricot tree was originated by us in the experimental orchard located near Modesto, Calif. It was selected from a number of seedlings grown from the seed of an open pollinated seedling with the field identification number 2W303. The seedling 2W303 originated from a large group of open pollinated Flaming Gold Apricot (U.S. Plant Pat. No. 2,822) seedlings.

ASEXUAL REPRODUCTION OF THE VARIETY

The present variety of apricot tree was asexually reproduced by budding, as performed at Modesto, Calif., and shows that said characteristics described above run true to the original tree and are identical in all respects.

SUMMARY OF THE VARIETY

Our new invention relates to a distinct variety of apricot tree which is of large size, vigorous, semi-spreading growth and a regular and productive bearer of medium size, very firm, yellow flesh, freestone fruit with good flavor and eating quality both fresh and canned. The fruit is further characterized by having high soluble solids (Average 15% Brix) and maintaining excellent texture, shape and appearance after being canned.

PHOTOGRAPHS OF THE VARIETY

The accompanying photographic reproductions show typical specimens of the foliage and fruit of our new apricot variety, with the upper and lower surface of the leaves being illustrated, also an exterior and sectional view of the fruit being shown with the stone remaining in place. These photographs were taken shortly after being picked at maturity (firm ripe) and the colors are as nearly true as reasonably possible in a color representation of this type.

DESCRIPTION OF THE VARIETY

The following is a detailed botanical description of our new and distinct variety of apricot tree, with color terminology (except those in common terms) in accordance with Reinhold Color Atlas by A. Kornerup and J. H. Wanscher.

Tree:
- *Size.*—Large.
- *Vigor.*—Vigorous.
- *Form.*—Semi-spreading.
- *Production.*—Productive.
- *Density.*—Medium dense.
- *Bearing.*—Regular.

Trunk:
- *Size.*—Medium stocky.
- *Surface.*—Medium to shaggy.
- *Color.*—Brown to grayish brown (8-F-3) to (8-F-5).

Branches:
- *Size.—Medium to stocky.*
- *Surface.*—Smooth to medium rough.
- *Lenticels.*—Numerous — large.
- *Color.*—Grayish brown (7-E-6) to reddish brown (8-E-6).

Leaves:
- *Size.*—Large. Average length — $4\frac{1}{4}''$ to $4\frac{3}{4}''$ Average width — $3\frac{1}{4}''$ to $3\frac{3}{4}''$.
- *Form.*—Ovate to orbicular. Pointed.
- *Texture.*—Smooth.
- *Margin.*—Serrate.
- *Petiole.*—Average length — $1\frac{1}{4}''$ Average width — $1/16''$.
- *Glands.*—Size — small. Globose. Number varies from 2 to 6. Average number 2. Located on lower portion of leaf blade and upper portion of petiole.
- *Color.*—Upper surface — dark green (27-F-8) to (28-F-8). Lower surface — grayish green (28-E-7) to (28-E-8).

Flower buds:
- *Size.*—Medium.
- *Length.*—Short.
- *Shape.*—Plump.

Flowers:
- *Blooming period.*—Feb. 23, 1987 to Feb. 28, 1987. Varies with climatic conditions.
- *Size.*—Medium to large.
- *Color.*—Pink — fades to white at petal fall.

*Pistil.*—Pubescent.
*Pollen.*—Present.

Fruit:
*Maturity when described.*—Firm ripe.
*Date of picking.*—June 3, 1987. Matures relatively uniform throughout the tree with enough firmness that it can be harvested in one picking or mechanically harvested.
*Size.*—Medium. Average diameter axially — $1\frac{7}{8}''$ to $2\frac{1}{8}''$. Average transversely in suture plane — $1\frac{3}{4}''$ to $2''$. Average diameter measured at right angles to suture plane — $1\frac{5}{8}''$ to $1\frac{3}{4}''$.
*Form.*—Globose — slightly compressed toward suture plane.
*Suture.*—Usually pronounced from stem to blossom end. Deeper near stem — terminates at blossom end.
*Apex.*—Rounded to slightly depressed.
*Base.*—Retuse.
*Ventral surface.*—Rounded, slightly lipped at stem end.
*Cavity.*—Rounded to elongated in suture plane, with suture showing on one side. Average depth — 3/16". Average breadth — $\frac{3}{8}''$.

Skin:
*Thickness.*—Medium.
*Texture.*—Medium — tenacious to flesh.
*Down.*—Scant — very short.
*Tendency to crack.*—None.
*Color.*—Apricot yellow to golden yellow (5-B-6) to (5-B-8).

Flesh:
*Texture.*—Very firm.
*Juice.*—Moderate.
*Fibers.*—Small size — tender.
*Amygdalin.*—Scant.
*Ripens.*—Uniform.
*Aroma.*—Pronounced.
*Flavor.*—Good — mild, sub-acid.

*Eating quality.*—Good.
*Color.*—Butter yellow to sunflower yellow (4-A-5) to (4-A-7).

Stone:
*Type.*—Freestone — some fruit have a slight amount of flesh adhering to the stone on stem end.
*Size.*—Medium. Average length — 1". Average width — $\frac{3}{4}''$. Average thickness —$\frac{3}{8}''$.
*Form.*—Ovid. Slightly cuspidate at apex.
*Base.*—Oblique.
*Tendency to split.*—None.
*Apex.*—Slightly cuspidate.
*Surface.*—Regularly pitted, only slightly throughout.
*Ridges.*—Sharp ridges only along ventral edge.
*Color.*—Light brown to brown (6-C-5) to (6-D-5).

Use: Culinary. Dessert.
*Market.*—Local and long distance.

Storage quality.—Excellent.

Shipping quality: Excellent.

The apricot tree and its fruit herein described may vary in slight detail due to cultural practices, soil types and climatic conditions under which the variety may be grown; the present description is that of the variety grown under the ecological conditions prevailing at Modesto, Calif.

We claim:

1. A new and distinct variety of apricot tree, substantially as illustrated and described which is a regular and productive bearer of medium size, very firm, freestone fruit that can be mechanically harvested without showing excessive bruising, and after being canned, maintaining excellent shape and texture with good flavor and eating quality; the fresh fruit is characterized by its uniform ripening, good flavor and eating quality and having excellent storage and shipping quality.

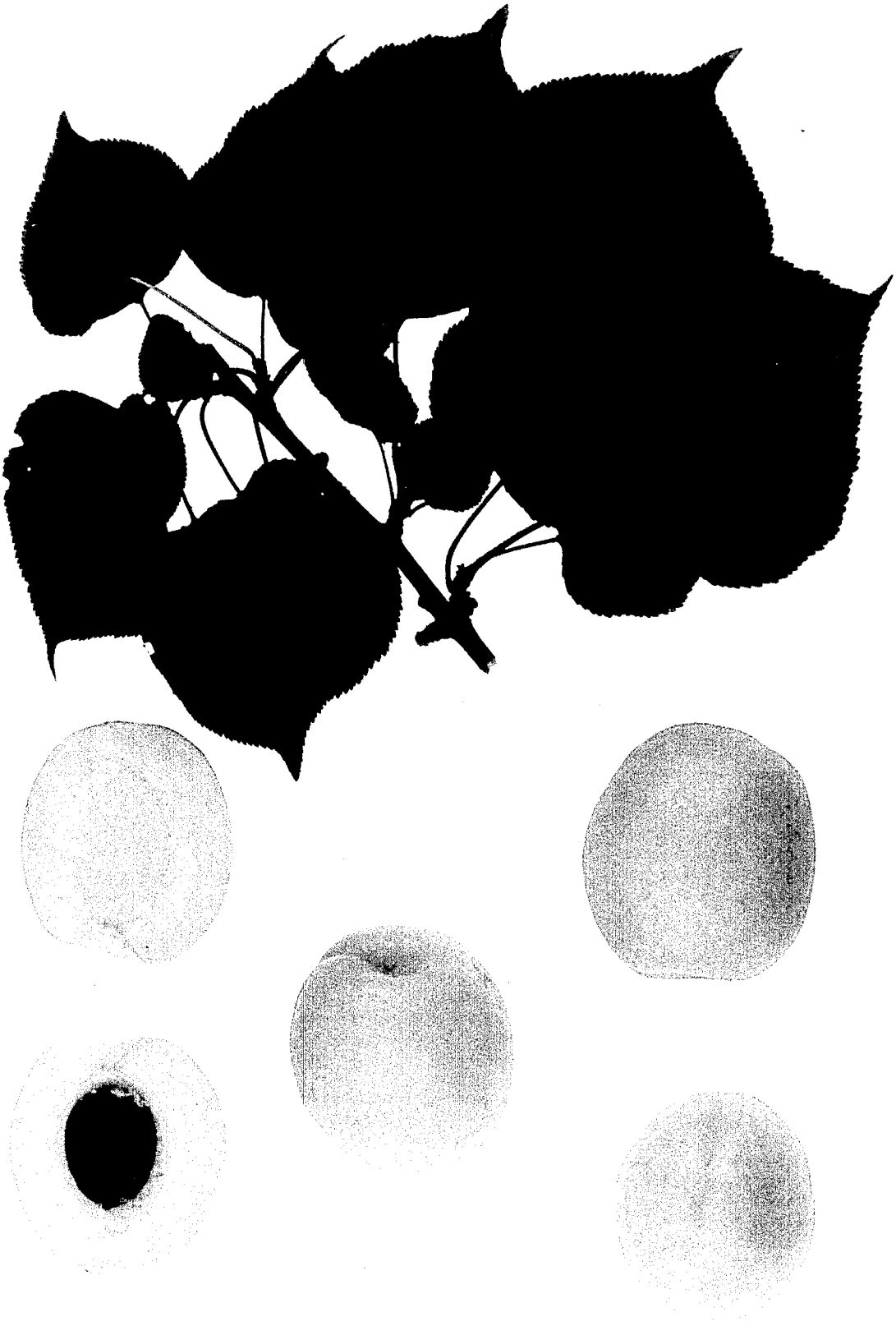

* * * * *